United States Patent [19]

Kondratenko et al.

[11] 4,156,019

[45] May 22, 1979

[54] METHOD FOR OBTAINING COMBINATION STARTERS FOR BULGARIAN YOGHURT

[75] Inventors: Maria S. Kondratenko; Stefka S. Kondareva; Bojana H. Gyosheva; Konstantza A. Vlaykovska; Irina G. Shishkova; Nevena N. Toteva; Lilyana V. Goranova, all of Sofia, Bulgaria

[73] Assignee: DSO Mlechna Promishlenost, Sofia, Bulgaria

[21] Appl. No.: 790,535

[22] Filed: Apr. 25, 1977

Related U.S. Application Data

[63] Continuation of Ser. No. 727,040, Sep. 27, 1976, abandoned, which is a continuation-in-part of Ser. No. 529,475, Dec. 4, 1974, abandoned.

[30] Foreign Application Priority Data

Dec. 4, 1973 [BG] Bulgaria ......................... 25150

[51] Int. Cl.² .............................................. A23C 9/12
[52] U.S. Cl. ........................................ 426/43; 426/61; 195/96; 195/111
[58] Field of Search .................... 426/34, 43, 61, 36; 195/96, 100, 111

[56] References Cited

U.S. PATENT DOCUMENTS 3,876,808  4/1975  Anderson ............................. 426/61

FOREIGN PATENT DOCUMENTS 2024018  4/1971  Fed. Rep. of Germany ............. 426/43

OTHER PUBLICATIONS

Webb et al., Byproducts from Milk, 2nd ed., The Ari Publishing Co., Inc., Westport, Conn. 1970, pp. 24–29.
Kosikomski, F., Cheese and Fermented Milk Foods, published by the author, Cornell University, Ithaca, N.Y., 1966, pp. 14–31.

*Primary Examiner*—David M. Naff
*Attorney, Agent, or Firm*—Armstrong, Nikaido, Marmelstein & Kubovcik

[57] ABSTRACT

Specific strains of the micro-organisms *Lactobacillus bulgaricum* and *Streptococcus thermophilus* are isolated, identified and purified and used for the preparation of starting materials for production of Bulgarian sour milk. The use of these micro-organisms is described together with procedures in the present invention for the production of Bulgarian sour milk having improved nutrient value and improved characteristic taste and flavor. Specified mixtures of the above micro-organisms can also be advantageously employed for this purpose.

10 Claims, No Drawings

METHOD FOR OBTAINING COMBINATION STARTERS FOR BULGARIAN YOGHURT

This is a continuation of application Ser. No. 727,040, filed Sept. 27, 1976, which is a continuation-in-part of application Ser. No. 529,475, filed Dec. 4, 1974, both now abandoned.

The present invention relates to new starting materials having greater activity and better production qualities, such as proteolytic activity and content of aromatic substances for the production of original Bulgarian sour milk. These starting materials are obtained with the newly isolated, purified and differentiated strains of *Str. thermophilus* and *Lb. bulgaricus*.

BACKGROUND OF THE INVENTION

It is known to produce Bulgarian sour milk using strains of *St. thermophilus* and *Lactobacillus bulgaricus* which establish a good symbiotic bond. Some of these micro-organisms have been reported in Bulgarian authorship certificate N10640, where a new technology for producing Bulgarian sour milk is described.

The present invention deals with new procedures for obtaining starting materials for sour milk, which is more active and having far better production qualities, for the production of original Bulgarian sour milk with higher nutritive qualities and characteristic taste and flavor.

DETAILED DESCRIPTION OF THE INVENTION

The principal feature of the present invention is to isolate, purify and differentiate new active strains of *St. thermophilus* and *Lactobacillus bulgaricus* which coexist well in order to obtain more active starting materials with better production qualities for the production of original Bulgarian sour milk. These procedures are carried out by isolation, purification and differentiation of the new strains of *St. thermophilus* and *Lactobacillus bulgaricus*, which can be distinguished by their biological and morphological characteristics, better proteolytic qualities (especially the strains of *Lactobacillus bulgaricus*), good coexistence and very good ability to form aromatic substances, as compared to known strains used for the same purpose, thereby resulting in more active combinations of starters having better production qualities for production of original Bulgarian sour milk from sheep or cow milk.

The new strains were deposited in the Bulgarian State Institute of Drug Control on Dec. 21, 1973, and in the Japanese Fermentation Research Institute of Industrial Technology with the following depository designations:

|   |   | Bulgarian Collection | Japanese Collection |
|---|---|---|---|
| 1) | *Lb. Bulgaricus* #5 | 151 | 3013 |
| 2) | *Lb. Bulgaricus* #26 | 152 | 3014 |
| 3) | *Lb. Bulgaricus* #37 | 153 | 3015 |
| 4) | *Lb. Bulgaricus* #144 | 154 | 3016 |
| 5) | *St. Thermophilus* #12 | 155 | 3009 |
| 6) | *St. Thermophilus* #14 | 156 | 3010 |
| 7) | *St. Thermophilus* #18 | 157 | 3011 |
| 8) | *St. Thermophilus* #22 | 158 | 3012 |

The above strains are isolated from natural starters, milk, herbs and raw cream. After being threefold purified, they are differentiated according to the following criteria defined by Zehleman, Berge, Rogasa, and Sharp: (1) defining the optimum temperature of growth and reduction of litmus milk, (2) organoleptic evaluation, (3) moment of coagulation and limit acidity, (4) morphologic characteristics of colonies and cells, (5) growth in milk with 0.1% methylene blue, (6) growth in broth (hydrolyzed milk or MRS) at pH 9.2 and 9.6, (7) growth in broth (hydrolyzed milk or MRS) with 2.4 and 6% bile, (8) growth in broth (hydrolyzed milk or MRS) with 2.4 and 6.5 salt, (9) development in esculin broth, (10) catalytical test, (11) formation of diacetyl, (12) carbohydrate fermentation, (13) proteolytic activity, expressed by number and quantity of free amino acids, (14) development in broth (MRS) and milk with phenol, (15) thermoresistance, (16) defining homo-and heterofermentability, (17) content of aromatic substances.

The strains are as follows:
1. *St. thermophilus* N, N12, 14, 18, 22

TABLE I

| Characteristics | N12 | N14 |
|---|---|---|
| Origin | v. Grashtizo-Bul. | v. Dalboki-Bul. |
| Morphology | | |
| a) Colony type at surface growth | small, round | round |
| b) Microscopic pattern | diplococci and short chains | |
| Organoleptic evaluation: | | |
| a) consistence | mucous | mucous |
| b) flavor | milksour | |
| c) taste | milksour | |
| Optimal growth temperature | 45° C. | 45° C. |
| Reduction | red reduction | — |
| Development at 10° C. | — | — |
| Development at 23° C. | 3 days | 3 days |
| Development at 32° C. | 14 hours | 14 hours |
| Development at 37° C. | 6.5 hours | 7 hours |
| Development at 50° C. | 12 hours | 12 hours |
| Limit Acidity | 124° T. (L+) | 123° T. (L+) |
| Growth in milk with 0.1% methylene blue | — | — |
| Moment of coagulation | 6–8 hours | 6–8 hours |
| Development in broth at pH 9.2 and 9.6 | — | — |
| Development in broth with 2.4 and 6% bile | — | — |
| Development in broth with 2.4 and 6.5% salt | — | — |
| Development in esculin broth | — | — |
| Catalytical test | — | — |
| Diacetyl formation (Foges-Proscauer) | — | — |
| Carbohydrate fermentation | ferment glucose, saccharose and lactos | |
| Thermoresistance | | |
| 63° - 30 min | + | + |
| 65° - 30 min | + | + |
| 75° - 30 min | — | — |

TABLE I

| Proleolytic activity expressed by number and quantity of free amino acids | N12 | | |
|---|---|---|---|
| | 8 h. (1) | 48 h. (2) | 15 d. (3) |
| 1. Cysteic acid | — | — | — |
| 2. X1, 2, 3, 4, 5, 6 | +++ | +++ | +++ |
| 3. Asparginic acid | .026 | .020 | .018 |
| 4. Methionine sulphone | — | — | — |
| 5. Threonine | .008 | .011 | .009 |
| 6. Serine | .015 | .017 | .019 |
| 7. Glutamic acid | .124 | .140 | .116 |
| 8. Proline | .050 | .045 | .064 |
| 9. Glycine | traces | .014 | .010 |
| 10. Alanine | .039 | .059 | .054 |
| 11. ½ Cystine | — | — | — |
| 12. X7 | + | + | + |
| 13. Valine | traces | traces | .005 |
| 14. X8 | traces | traces | traces |

TABLE I-continued

| Proleolytic activity expressed by number and quantity of free amino acids | N12 | | |
|---|---|---|---|
| | 8 h. (1) | 48 h. (2) | 15 d. (3) |
| 15. Methionine | traces | traces | traces |
| 16. Isoleucine | traces | traces | traces |
| 17. Leucine | traces | traces | traces |
| 18. X9 | + | + | + |
| 19. Tyrosine | — | — | traces |
| 20. Phenylalanine | — | — | traces |
| 21. X10, 11, 12 | +++ | +++ | +++ |
| 22. Lysine | traces | traces | traces |
| 23. Histidine | traces | traces | 0.013 |
| 24. Ammonia | + | + | + |
| 25. Arginine | traces | — | traces |

Note:
The amino acids quantity is in micromoles in 1 ml coagulated milk
X = unknown amino acids

TABLE I

| Proteolytic activity expressed by number and quantity of free amino acids | N14 | | |
|---|---|---|---|
| | 8 h. (4) | 48 h. (5) | 15 d. (6) |
| 1. Cysteic acid | — | — | — |
| 2. X1, 2, 3, 4, 6 | +++ | +++ | +++ |
| 3. Asparginic acid | .021 | .018 | .019 |
| 4. Methionine sulphone | | | |
| 5. Threonine | .006 | .009 | .011 |
| 6. Serine | .018 | .024 | .018 |
| 7. Glutamic acid | .096 | .110 | .121 |
| 8. Proline | .056 | .051 | .061 |
| 9. Glycine | .010 | .015 | .011 |
| 10. Alanine | .023 | .047 | .057 |
| 11. ½ Cystine | — | — | — |
| 12. X7 | + | + | + |
| 13. Valine | traces | traces | 0.006 |
| 14. X8 | traces | traces | traces |
| 15. Methionine | traces | traces | traces |
| 16. Isoleucine | traces | traces | traces |
| 17. Leucine | traces | traces | traces |
| 18. X9 | + | + | + |
| 19. Tyrosine | — | — | — |
| 20. Phenylalanine | — | — | traces |
| 21. X10, 11, 12 | traces | traces | +++ |
| 22. Lysine | traces | + | + |
| 23. Histidine | traces | traces | .015 |
| 24. Ammonia | + | + | + |
| 25. Arginine | traces | — | — |

Note: The amino acids quantity is in micromoles in 1 ml coagulated milk
X = unknown amino acids

TABLE II

| Characteristics | N18 | N22 |
|---|---|---|
| Origin | v. Dalboki-Bul. | v. Preslavez-Bul. |
| Morphology | | |
| a) Type of colony at surface growth | small, round diplococci and short chains | small, round |
| b) Microscopical pattern | | |
| Organoleptic evaluation | | |
| a) consistence | like cream or milk | |
| b) flavor | milk sour | |
| c) taste | milk sour | |
| Optimal growth temperature | 45° C. | 45° C. |
| Reduction | red reduction | |
| Development at 10° C. | — | — |
| Development at 23° C. | 3 days | 4 days |
| Development at 32° C. | 12 hours | 15 hours |
| Development at 37° C. | 6.30 hours | 15 hours |
| Development at 50° C. | 12 hours | 15 hours |
| Limit Acidity | 120°T. (L+) | 144° T. (L+) |
| Growth in milk with 0.1% methylene blue | — | — |
| Moment of coagulation | 6-8 hours | 6-8 hours |
| Development in broth with 2.4 and 6% bile | — | — |
| Development in broth at pH 9.2 and 9.6 | — | — |
| Development in broth with 2.4 and 6.5% salt | — | — |
| Development in esculin broth | — | — |
| Catalytical test | — | — |
| Diacetyl formation (Foges-Proscauer) | — | — |
| Carbohydrates fermentation | ferment glucose, saccharose and lactose | |
| Thermoresistance | | |
| 63° - 30 min | + | + |
| 65° - 30 min | + | + |
| 75° - 30 min | — | — |

TABLE II

| Proteolytic activity expressed by type and quantity of free amino acids | N18 | | |
|---|---|---|---|
| | 8 h. (1) | 48 h. (2) | 15 d. (3) |
| 1. Cysteic acid | — | — | — |
| 2. X1, 2, 3, 4, 6 | +++++ | +++++ | traces |
| 3. Asparginic acid | .023 | .023 | .017 |
| 4. Methionine sulphon | — | — | — |
| 5. Threonine | .011 | .008 | .011 |
| 6. Serine | .108 | .021 | .015 |
| 7. Glutamic acid | .060 | .061 | .031 |
| 8. Proline | traces | .035 | .055 |
| 9. Alanine | — | .035 | .032 |
| 10. Glycine | .018 | .013 | .011 |
| 11. ½ Cystine | — | — | — |
| 12. X 7 | + | + | + |
| 13. Valine | traces | traces | .008 |
| 14. Methionine | traces | traces | + |
| 15. Isoleucine | — | — | .006 |
| 16. Leucine | traces | traces | .005 |
| 17. X9 | traces | + | + |
| 18. Tyrosine | — | — | traces |
| 19. Phenylalanine | — | — | traces |
| 20. X10, 11, 12 | traces | traces | +++ |
| 21. Lysine | traces | traces | + |
| 22. Histidine | traces | traces | .015 |
| 23. Ammonia | + | + | + |
| 24. Arginine | + | — | — |

TABLE II

| Proteolytic activity expressed by type and quantity of free amino acids | N22 | | |
|---|---|---|---|
| | 8 h. (4) | 48 h. (5) | 15 d. (6) |
| 1. Cysteic acid | — | — | — |
| 2. X1, 2, 3, 4, 6 | | | |
| 3. Asparginic acid | + | — | — |
| 4. Methionine sulphone | — | — | — |
| 5. Threonine | — | — | + |
| 6. Serine | + | ++ | ++ |
| 7. Glutamic acid | + | | + |
| 8. Proline | + | | ++ |
| 9. Alanine | | | traces |
| 10. Glycine | + | | ++ |
| 11. ½ Cystine | — | — | — |
| 12. X7 | | | |
| 13. Valine | — | — | — |
| 14. Methionine | — | — | — |
| 15. Isoleucine | + | | + |
| 16. Leucine | | | |
| 17. X 9 | | | |
| 18. Tyrosine | — | — | — |
| 19. Phenylalanine | — | — | — |
| 20. X10, 11, 12 | — | — | — |
| 21. Lysine | — | — | — |
| 22. HIstidine | — | — | — |
| 23. Ammonia | | | |
| 24. Arginine | | | |

2. *Lactobacillus bulgaricum* N, N5, 37, 26 and 144

TABLE III

| Characteristics | N5 | N37 |
|---|---|---|
| Origin | v. Dalboki-Bul | v. Hrishtene-Bul |
| Morphology | | |
| a) Type of colony | R colonies | S colonies |
| Microscopical picture | short rods with volutine grains | |
| Cell size | 5–10 μ | 4–8 μ |
| Organoleptic evaluation: | | |
| a) consistence | slightly grainlike | slightly grainlike |
| b) flavor | lactic acid | specific |
| c) taste | characteristic lactic acid taste | |
| Optimal temperature growth | 45° C. | 45° C. |
| Development at 15° C. | — | — |
| Development at 32°C. | 23 hours | 20 hours |
| Development at 37° C. | 11 hours | 10 hours |
| Development at 50° C. | 9.30 hours | 12.30 hours |
| Moment of coagulation | 7–8 hours | 7–8 hours |
| Limit acidity | 141° T. (D—) | 176° T. (D—) |
| Growth in milk with 0.1% methylene blue | — | — |
| Development in broth at pH 9.2 | — | — |
| Development in broth with 2.4 and 6% bile | — | — |
| Development in broth with 2.4 and 6.5% salt | 2%+ | 2%+ |
| Development in esculin broth | | |
| Catalytical test | — | — |
| Reaction for homo- and heterofermentability | | |
| Ammonia formation from argine | homofermentatine — | — |
| Thermoresistance | | |
| 63° - 30 min | + | + |
| 65° - 30 min | + | + |
| 70° - 30 min | — | — |
| Development in milk and broth with phenol: | | |
| a) In MRS broth with | | |
| 0.1% phenol | + | + |
| 0.2% phenol | — | — |
| b) milk with | | |
| 0.1% phenol | + | + |
| 0.2% phenol | + | + |
| 0.3% phenol | + | + |
| 0.4% phenol | — | — |
| Carbohydrates fermentation: | ferment glucose, saccharose lactose | |

TABLE III

| Proteolytic activity expressed by type and quantity of free amino acids | N5 | | |
|---|---|---|---|
| | 8 h. (1) | 48 h. (2) | 15 d. (3) |
| 1. Cysteic acid | — | — | — |
| 2. X1, 2, 3, 4, 5, 6 | +++++ | +++++ | ++++ |
| 3. Asparginic acid | .034 | .179 | .134 |
| 4. Methionine sulphon | — | — | — |
| 5. Threonine | .087 | .339 | .225 |
| 6. Serine | .188 | .522 | .358 |
| 7. Glutamine acid | .228 | 1.037 | .719 |
| 8. Proline | .385 | .772 | .575 |
| 9. Glycine | .069 | .183 | .121 |
| 10. Alanine | .164 | .135 | .147 |
| 11. ½ Cystine | — | — | — |
| 12. X7 | traces | traces | traces |
| 13. Valine | .224 | .583 | .375 |
| 14. Methionine | .049 | .113 | .079 |
| 15. Isoleucine | .089 | .321 | .246 |
| 16. Leucine | .138 | .511 | .353 |
| 17. X9 | + | + | + |
| 18. Tyrosine | .054 | .145 | .106 |
| 19. Phenylanine | .028 | .178 | .125 |
| 20. X10, 11 | ++ | +tr. | ++ |
| 21. Lysine | .173 | .268 | .210 |
| 22. Histidine | .080 | .125 | .074 |
| 23. Ammonia | + | + | + |
| 24. Arginine | .074 | .176 | .120 |

Note: The free amino acids quantity is in micromoles in 1 ml coagulated milk

TABLE III

| Proteolytic activity expressed by type and quantity of free amino acids | N37 | | |
|---|---|---|---|
| | 8 h. (4) | 48 h. (5) | 15 d. (6) |
| 1. Cysteic acid | — | — | — |
| 2. X1, 2, 3, 4, 5, 6 | +++++ | +++++ | ++++ |
| 3. Asparginic acid | .043 | .084 | .137 |
| 4. Methionine sulphon | — | — | — |
| 5. Threonine | .077 | .102 | .150 |
| 6. Serine | .290 | .303 | .447 |
| 7. Glutamine acid | .416 | .563 | .745 |
| 8. Proline | .680 | .669 | .959 |
| 9. Glycine | .015 | .038 | .060 |
| 10. Alanine | .026 | .099 | .284 |
| 11. ½ Cystine | traces | — | — |
| 12. X7 | traces | traces | traces |
| 13. Valine | .258 | .269 | .382 |
| 14. Methionine | traces | .023 | .045 |
| 15. Isoleucine | .052 | .095 | .127 |
| 16. Leucine | .083 | .147 | .191 |
| 17. X9 | traces | traces | traces |
| 18. Tyrosine | traces | .015 | .021 |
| 19. Phenylanine | .028 | .057 | .076 |
| 20. X10, 11 | +tr. | ++ | ++ |
| 21. Lysine | .015 | .053 | .071 |
| 22. Histidine | .058 | .065 | .084 |
| 23. Ammonia | + | + | + |
| 24. Arginine | .034 | .048 | .070 |

Note: The free amino acids quantity is in micromoles in 1 ml coagulated milk

TABLE IV

| Characteristics | N144 | N26 |
|---|---|---|
| Origin | v.Novoselo-Bul | v. Grashiza-Bul |
| Morphology | | |
| a)Colony type | R colonies | S colonies |
| Microscopical pattern | short rods with volutine grains | |
| Cell size | 5–8 μ | 5–10 μ |
| Organoleptic evaulation | slightly granlike | |
| a) consistence | | |
| b) flavor | milk sour | specific |
| c) taste | characteristic lactic acid taste | |
| Optimal growth temperature | 45° C. | 45° C. |
| Development at 15° C. | | |
| Development at 32° C. | 20 hours | 19.30 hours |
| Development at 37° C. | 11 hours | 10 hours |
| Development at 50° C. | 7-8 40 hours | 6-8 hours |
| Limit acidity | 189° T. (D—) | 225° T. (D—) |
| Development in milk with 0.1% methylene blue | — | — |
| Development in broth at pH 9.2 | — | — |
| Development in broth with 2.4 and 6% bile | — | — |
| Development in broth with 2.4 and 6.5% salt | 2%+ | 2%+ |
| Development in esculin broth | — | — |
| Catalytical test | — | — |
| Reaction for homo- and heterofermentability | homofermentative for all | |
| Ammonia formation from arginine | — | |
| Thermoresistance | | |
| 63° C. - 30 min | + | + |
| 65° C. - 30 min | + | + |
| 70° C. - 30 min | — | — |
| Development in milk and broth with phenol: | | |

TABLE IV-continued

| Characteristics | N144 | N26 |
|---|---|---|
| a) with MRS broth with | | |
| 0.1% phenol | + | + |
| 0.2% phenol | + | + |
| b) milk with | | |
| 0.1% phenol | + | + |
| 0.2% phenol | + | + |
| 0.3% phenol | + | + |
| 0.4% phenol | − | − |
| Carbohydrates fermentation: | ferment glucose and lactose | |

TABLE IV

| Proteolytic activity expressed by type and quantity of free amino acids | N144 | | |
|---|---|---|---|
| | 8 h. (1) | 48 h. (2) | 15 d. (3) |
| 1. Cysteic acid | − | − | − |
| 2. X1, 2, 3, 4, 5, 6 | +++++ | +++++ | +++++ |
| 3. Asparginic acid | .066 | .098 | .200 |
| 4. Methlonone sulphon | − | − | − |
| 5. Threonine | .096 | .128 | .199 |
| 6. Serine | .268 | .312 | .486 |
| 7. Glutamic acid | .835 | .825 | 1.380 |
| 8. Proline | .768 | .757 | 1.320 |
| 9. Glycine | .020 | .049 | .082 |
| 10. Alanine | .041 | .134 | .319 |
| 11. ½ Cystine | − | − | − |
| 12. X7 | traces | traces | traces |
| 13. Valine | .356 | .345 | .576 |
| 14. Methionine | .041 | .041 | .076 |
| 15. Isoleucine | .168 | .173 | .304 |
| 16. Leucine | .198 | .217 | .383 |
| 17. X9 | traces | traces | traces |
| 18. Tyrosine | .050 | .050 | .085 |
| 19. Phenylalanine | .067 | .084 | .148 |
| 20. X10, 11 | ++ | ++ | ++ |
| 21. Lysine | .185 | .177 | .312 |
| 22. Histidine | .161 | .104 | .184 |
| 23. Ammonia | + | + | + |
| 24. Arginine | .077 | .088 | .153 |

TABLE IV

| Proteolytic activity expressed by type and quantity of free amino acids | N26 | | |
|---|---|---|---|
| | 8 h. (4) | 48 h. (5) | 15 d. (6) |
| 1. Cysteic acid | | | |
| 2. X1, 2, 3, 4, 5, 6 | | | |
| 3. Asparginic acid | ++ | | + |
| 4. Methlonone sulphon | − | − | − |
| 5. Threonine | ++ | | + |
| 6. Serine | + | | + |
| 7. Glutamic acid | +++++ | | ++ |
| 8. Proline | +++++ | | ++++ |
| 9. Glycine | + | | + |
| 10. Alanine | ++ | | ++ |
| 11. ½ Cystine | | | |
| 12. X7 | | | |
| 13. Valine | ++++++ | | ++++++ |
| 14. Methionine | ++++++ | | ++++++ |
| 15. Isoleucine | +++ | | ++ |
| 16. Loucine | | | |
| 17. X9 | | | |
| 18. Tyrosine | +++ | | ++ |
| 19. Phenylalanine | ++ | | |
| 20. X10, 11 | | | |
| 21. Lysine | +++ | | +++ |
| 22. Histidine | ++ | | |
| 23. Ammonia | | | |
| 24. Arginine | +++ | | + |

Combination of Two Microorganisms

TABLE V

| Characteristics | 5-12 | 5-22 | 37-12 | 37-18 |
|---|---|---|---|---|
| Microscopical pattern | Diplococci Medium-long, dense rods, in single pairs or small chains | | | |
| Time of coagulation: | for all 2 hours at +45° C. (1 ml for 100 ml) for all 3.30 h. (0.1 g dry for 100 ml) | | | |
| Type of coagulum: | | | | |
| a) consistence | dense for all | | | |
| b) fracture | smooth-flittering for all | | | |
| c) taste and flavor | specific, well expressed for all | | | |
| Free amino acids: | | | | |
| Leucine | | | +++ | +++ |
| Phenyl alanine | | | | |
| Valine methionine | +++++++ | +++++ | | traces |
| Tyrosine | ++ | +++ | | + |
| Aminobutyric acid | + | + | | |
| Proline | ++++ | +++++ | +++ | +++++ |
| Alfa alanine | +++ | +++ | +++ | +++++ |
| Tronine | + | + | | |
| Glutamine acid | ++ | +++++ | ++ | +++ |
| Glycine serine | | | ++ | |
| Serine | | | | + |
| Asparginic acid | | | | |
| Aspargine | | | traces | |
| Histidine | | | | |
| Lysine | ++ | + | | |
| Ornithine | | + | | |
| Cystedine | | | +++ | |
| Oxiproline | | | | + |
| Tryptophan | | | | |
| Activity: | | | | |
| a) Liquid combination starter | | | | |

TABLE V-continued

| Characteristics | 5-12 | 5-22 | 37-12 | 37-18 |
|---|---|---|---|---|
| St. Thermophilus | 575 mln/ml | 550 mln/ml | 962 mln/ml | 580 mln/ml |
| Lb. Bulgaricum | 211 mln/ml | 242 mln/ml | 309 mln/ml | 250 mln/ml |
| b) Dry combination starter (lioph) St. Thermophilus | 4,500mln/g | 4.500 mln/g | 4.500 mln/g | 2.500 mln/g |
| Lb. Bulgaricum | 45 mln/g | 45 mln/g | 9.5 mln/g | 9.5 mln/g |
| Volatile acids | 15.60 | 15.40 | 18.20 | 15.60/ | mln=million

TABLE VI

| Characteristics | 26-12 | 144-12 | 144-14 |
|---|---|---|---|
| Microscopic pattern | Diplococci, medium-long, dense rods, single, in pairs or short chains | | |
| Time of Coagulation | For all 2 hours (1 ml for 100 ml) 3.30 h. (0.1 g dry for 10 ml) | | |
| Type of coagulum: | | | |
| a) consistency | dense for all | | |
| b) fracture | smooth-glittering for all | | |
| c) taste and flavor | specific, well expressed for all | | |
| free amino acids: | | | |
| Leucine | +++ | + | ++ |
| Phenyl alanine | | + | + |
| Tryptophan | | | |
| Valin methionine | ++ | +++++ | +++ |
| Tyrosine | ++ | ++ | + |
| Aminobutyric acid | | + | ++ |
| Proline | ++++ | +++++ | ++++ |
| Alfa alanine | +++ | +++ | ++++ |
| Trionine | | | |
| Glutamine acid | + | ++++ | ++++ |
| Glycine | + | | + |
| Serine | | | |
| Asparginic acid | traces | | |
| Aspargine | | traces | |
| Histidine | | | |
| Lysine | traces | | |
| Ornethine | | | |
| Cystedine | | | |
| Oxyproline | | | |
| Activity: | | | |
| a) Liquid combination Starter | | | |
| St. Thermophilus | 1.983mln/ml | 1.300mln/ml | 783mln/ml |
| Lb. Bulgaricum | 497mln/ml | 213mln/ml | 383mln/ml |
| b) dry combination starter (lioph) St. Thermophilus | 2.500mln/g | 4.500mln/g | 4.500mln/g |
| Lb. Bulgaricum | 9.5 mln/g | 9.5 mln/g | 10 45 mln/g |
| Volatile acids | 15.60 | 17.60 | 15.20 |

Note:
Combination starters 144-12 and 144-14 are able to produce mucous cosistency under special technologic circumstances and therefore they are used for producing reservoir sour milk The strains of *Streptococcus thermophilus* and *Lactobacterium bulgaricum* described above, produced 300 combination starters in the following way: each of a number of retorts containing 100 ml sterile cow milk at 45° C. (±1° C.) were inoculated with a combination starter consisting of 1 ml of a strain of *Str. thermophilus* and 1 ml of a strain of *Lb. bulg.* The inoculated milk was thermostated at +45° C. and the coagulation time observed. The combination starters causing coagulation in two-hours time were examined under a microscope for normal cell morphology of both strains. Immediately after examination, 100 ml sterile sheep milk or a mixture of sheep and cow milk at a ratio 1:1 were inoculated each with 1% of an approved combination starter. The latter were subcultured in the same medium in the course of four months every day and in the course of another two—every week. The inoculation time of each reinoculation as well as the microscopic pattern and ratio between the strains of *Str. therm.* and *Lb. bulg.* were regularly observed throughout the whole six month period. If the cells of both micro-organisms did not change morphologically throughout this period and the ration of the combination starters observed remained the same, they were used for production tests. This was preceded by degustation evaluation of sour milk prepared with the approved combination starters under laboratory conditions after the criteria further cited.

Seven combination starters out of 300 combination starters were selected on the basis of a satisfactory coexistence and a stable ratio.

Evaluation of the new combination starters for sour milk is carried out according to the following criteria:
(1) microscopic pattern of the combination starters which immediately after coagulation were placed in a refrigerator at +4° C. for 24 hours. (a) *Streptococcus thermophilus* well shaped and well dyed diplococci, (b) *Lactobacillus bulgaricus* dense, clear cut small rods, single, in couples or small chains. The ratio between the two micro-organisms should vary from 1:3–1:10;
(2) the coagulation time was observed at +45° C. (±1° C.) using 1% combination starter—2 hours.
(3) organoleptic evaluation of sour milk samples prepared from homogenized whole cow milk pasteurised at 95° C. with holding time of 30 minutes. The samples were then cooled and inoculated at 45° C. each with 1% of an approved combination-starter followed by thermostating them at 45° C. After coagulation, the samples were left at indoors temperature until the acidity reached 75° T, whereafter they were put in a refrigerator at +4° C. They were tasted in 24 hours time after tempering them to indoors temperature. The organoloptic evaluation disclosed the characteristics below: type of coagulum, color, consistence and structure, fracture, taste and flavor. In addition, the volatile acids were defined, the acidity in grades Törner, the free amino acids-qualitatively or quantitatively, the aromatic substances and the activity of the combination starters in liquid and dry lyophilized form. The activity is determined on the basis of: (a) through the method of limiting dilution and recording the number of *Streptococcus thermophilus* and *Lactobacillus bulgaricus* as well as their ratio after McKredy and (b) time of coagulation lyophilized combination starter (0.1 g in 100 ml sterile cow milk-whole milk or skimmed) for 3½ hours, liquid combination starter (1 ml in 100 ml of sterile whole or skimmed cow milk)—2 hours.

The sour milk combination starters NN5-12, 5-22, 37-12, 37-18, 26-12, 144-12 and 144-14 were characterized by the criteria given in the tables.

What is claimed is:

1. Method for obtaining combination starters for the production of Bulgarian sour milk which comprises the following steps:
   (a) innoculating each of a plurality of portions of sterile cow milk with a combination starter containing microorganism strains selected from the group consisting of *Lactobacillus bulgaricus* Numbers 5, 26, 37 and 144 and another microorganism strain selected from the group consisting of *Streptococcus thermophilus* Numbers 12, 14, 18 and 22 to form a plurality of inoculums;
   (b) cultivating the plurality of inoculums at 44° to 46° C. to cause coagulation and observing the coagulation times;
   (c) subsequent to said coagulating, selecting from the plurality of coagulated inoculums, combination starters that cause said coagulation in about two hours and have desired cellular configuration and desired ratio between said Lactobacillus and Streptococcus strains;
   (d) subsequent to said selecting, inoculating with about 1% of said selected combination starters a plurality of portions of sterile sheep milk or a mixture of sheep and cow milk in a ratio of 1:1 to form a plurality of inoculums containing said selected combination starters,
   (e) subsequent to step (d), carrying out subculturing of said plurality of inoculums by daily inoculation in said sheep milk or said mixture of each said selected combination starter innoculated in (d) during the first four months and weekly for two additional months;
   (f) selecting from the combination starters subcultured in step (e) the combination starters that maintain consistant desired cellular configuration and consistant desired ratio between said Lactobacillus and Streptococcus strains throughout said subculturing; and
   (g) testing the combination starters selected in step (f) for producing Bulgarian sour milk having desired properties.

2. Method in compliance with claim 1 in which the ratio of the two strains in step (f) is 1:3 to 1:10.

3. Method according to claim 1 wherein the combination starter contains *Lactobacillus bulgaricus* Number 5 and *Streptococcus thermophilus* Number 12.

4. Method according to claim 1 wherein the combination starter contains *Lactobacillus bulgaricus* Number 5 and *Streptococcus thermophilus* Number 22.

5. Method according to claim 1 wherein the combination starter contains *Lactobacillus bulgaricus* Number 37 and *Streptococcus thermophilus* Number 18.

6. Method according to claim 1 wherein the combination starter contains *Lactobacillus bulgaricus* Number 37 and *Streptococcus thermophilus* Number 12.

7. Method according to claim 1 wherein the combination starter contains *Lactobacillus bulgaricus* Number 144 and *Streptococcus thermophilus* Number 12.

8. Method according to claim 1 wherein the combination starter contains *Lactobacillus bulgaricus* Number 144 and *Streptococcus thermophilus* Number 14.

9. Method according to claim 1 wherein the combination starter contains *Lactobacillus bulgaricus* Number 26 and *Streptococcus thermophilus* Number 12.

10. A method of making sour milk using a combination starter produced by the method of claim 1.

* * * * *